United States Patent
McClelland et al.

(10) Patent No.: US 8,620,405 B2
(45) Date of Patent: Dec. 31, 2013

(54) SKIN MARKER

(75) Inventors: Brian McClelland, County Antrim (GB); Robert John Winder, Northern Ireland (GB); Justin Dominic Martin Magee, County Londonderry (GB); Paul McCarron, County Down (GB)

(73) Assignee: University of Ulster, County Londonderry (GB)

( * ) Notice: Subject to any disclaimer, the term of this patent is extended or adjusted under 35 U.S.C. 154(b) by 61 days.

(21) Appl. No.: 13/318,806

(22) PCT Filed: May 7, 2010

(86) PCT No.: PCT/EP2010/002814
§ 371 (c)(1),
(2), (4) Date: Nov. 4, 2011

(87) PCT Pub. No.: WO2010/127870
PCT Pub. Date: Nov. 11, 2010

(65) Prior Publication Data
US 2012/0059244 A1    Mar. 8, 2012

(30) Foreign Application Priority Data

May 8, 2009  (GB) .................................. 0907874.2
Sep. 14, 2009 (GB) .................................. 0916099.5

(51) Int. Cl.
*A61B 5/055* (2006.01)
*H05G 1/28* (2006.01)

(52) U.S. Cl.
USPC ............................ 600/414; 600/426; 378/163

(58) Field of Classification Search
USPC ...................... 600/414, 426; 378/37, 162, 163
See application file for complete search history.

(56) References Cited

U.S. PATENT DOCUMENTS

| 5,368,030 | A | 11/1994 | Zinreich et al. |
| 5,469,847 | A | 11/1995 | Zinreich et al. |
| 6,978,167 | B2 * | 12/2005 | Dekel et al. ................... 600/426 |
| 2004/0116802 | A1 | 6/2004 | Jessop et al. |
| 2009/0022272 | A1 | 1/2009 | Joseph et al. |

FOREIGN PATENT DOCUMENTS

EP       0228692 A2    7/1987

OTHER PUBLICATIONS

International Search Report of the International Searching Authority from corresponding Patent Cooperation Treaty (PCT) Application No. PCT/EP2010/002814, mailed Jul. 23, 2010.

* cited by examiner

*Primary Examiner* — Michael Rozanski
(74) *Attorney, Agent, or Firm* — Gardner Linn Burkhart & Flory, LLP

(57) ABSTRACT

A skin marker for providing a reference point for a plurality of different medical imaging procedures, said marker incorporating one or more substances having one or more of radiance and/or hydration and/or radiopaque and/or radio luminescent and/or radioactive properties for detection by X-ray and/or Computer Tomography (CT) and/or MRI and/or Ultrasonic scanning processes and/or Positron Emission Tomography (PET), and one or more markings recognizable by an optical imaging process such as 3D surface scanning.

20 Claims, 2 Drawing Sheets

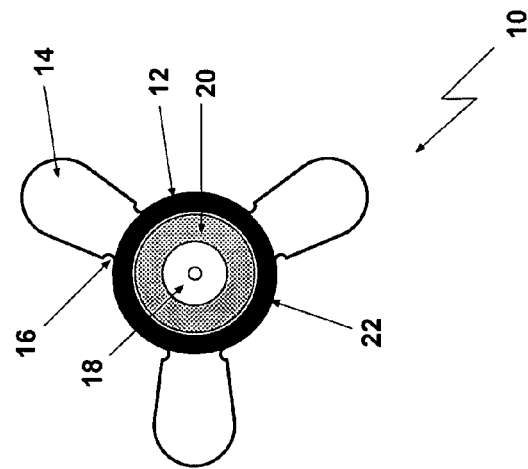
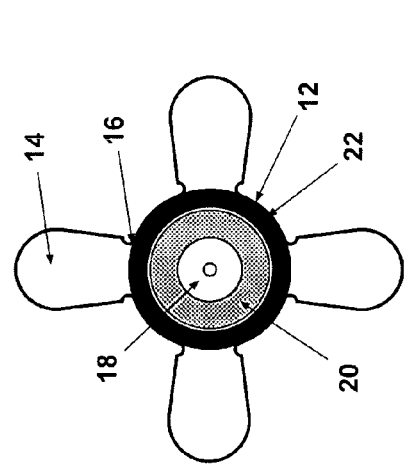
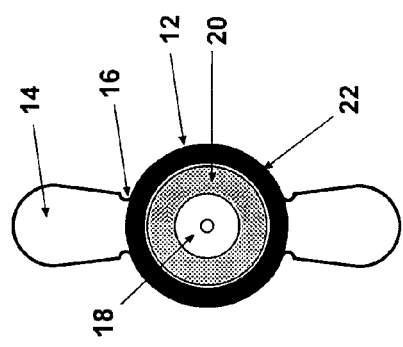
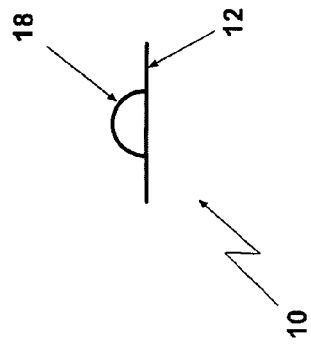

Section A-A

SKIN MARKER

FIELD OF THE INVENTION

This invention relates to a skin/body marker and in particular to a trans-modal/multi-modal skin marker for use as a reference marker for mapping anatomical landmarks when using a range of invasive and non-invasive imaging methods. Applications may include medical imaging processes for measurement, diagnostic and therapeutic procedures, posture mapping for spinal analysis and biomechanics purposes and as a measurement reference for anthropometrics, sports science, fitness and fashion industries.

BACKGROUND OF THE INVENTION

A variety of imaging techniques are available for imaging different anatomical structures of the body, such as X-ray imaging, typically used for imaging bones, Computer Tomography (CT), typically used for generating a three-dimensional image of the inside of an object from a large series of two-dimensional X-ray images taken around a single axis of rotation, Magnetic Resonance Imaging (MRI), or Nuclear Magnetic Resonance Imaging (NMRI), used most commonly to visualize the internal structure and function of the body, including soft tissues as well as bones, Diagnostic sonography (ultrasound scanning), used to visualize subcutaneous body structures including tendons, muscles, joints, vessels and internal organs for possible pathology or lesions and Positron Emission Tomography (PET), where a three-dimensional image or picture of functional processes in the body is produced by creating images of the passage of a radioactive tracer through the body.

It is often desirable to register images produced by such modalities, for example for full spine imaging, and there is an emerging trend to register images produced by different techniques to each other. To do this, reference points are required to register the various images. Different skin markers are available to suit each imaging technique. However, these markers are all different and may not be transferable between modalities, meaning that they need to be removed and alternative ones replaced between different scanning operations, leading to a risk of placement error and mis-registration of the various images produced.

Many markers also have difficulty in attaching to the skin, due to hair and moisture, and some have very small surface areas, increasing this problem. Furthermore, none of the known markers are suitable for reliable recognition by 3D surface scanning technologies, which are increasingly used in volumetric analysis and surface profiling/measurement operations.

SUMMARY OF THE INVENTION

According to one aspect of the present invention, there is provided a skin marker for providing a reference point for a plurality of different medical imaging procedures, said marker incorporating one or more substances having one or more of radiance and/or hydration and/or radiopaque and/or radio luminescent and/or radioactive properties for detection by X-ray and/or Computer Tomography (CT) and/or MRI and/or Ultrasonic scanning processes and/or Positron Emission Tomography (PET), and one or more markings recognisable by an optical imaging process such as 3D surface scanning.

In one embodiment said substance may comprise a radiopaque material having a radiographic density sufficient to produce a discernable shadow on a radiographic image.

In one embodiment said markings may comprise at least one first marking recognisable by Moiré Fringe 3D scanning processes or other optical scanning processes and at least one second marking recognisable by a colour recognition imaging process. Said first marking may comprise a substantially non-reflective image, such as a matt black printed image. Said second marking may comprise a coloured image, for example a blue or green image.

The marker may include a 3D surface formation. Such surface formation may be adapted to be recognisable by ultrasound and 3D surface scanning processes, including photogrammetry and laser scanning, or other optical imaging processes and/or may comprise a chamber or reservoir within which said one or more substances may be located.

Preferably said one or more substances are encapsulated within said 3D surface formation. In one embodiment said 3D surface formation comprises a hollow body containing a liquid, semi-liquid or solid material, said material containing and/or comprising said one or more substances. The material may comprise an oil based liquid (such as vitamin E fish oils), an oil-based semi-solid material or a gelled material. Such gelled material may comprise either an oil or aqueous base having a rheological structure, which may be achieved by way of high polymeric concentration, incorporation of stiffening agents, induced hydrogen bonding or covalent cross-linking using molecular or ionic species. One suitable material may be a hydrogel, such as a PVA (poly vinyl alcohol) hydrogel.

In one embodiment said 3D surface formation comprises a dome shaped member defining a substantially hemi-spherical surface formation. Preferably said dome shaped member is located on a central portion of the marker. At least a portion of the dome shaped member may be optically transparent to define a magnifying lens to assist correct location of the marker on the skin. Alternatively the dome may be coloured and/or possess markings to provide enhanced visibility.

Said one or more markings may comprise one or more concentric rings located around said dome shaped member.

The skin marker may further include two or more tabs or wings, such as tabs or wings extending radially from said central portion of the marker, to enable the marker to be attached to the body. Said tabs or wings may be provided with a suitable adhesive, which may be covered by a releasable cover material, and/or may define locations or carriers for the attachment of surgical tape to enable the marker to be affixed to the skin. Each tab may have a semi-circular indent at their respective hinge point to allow better flexion and positioning over the human anatomy.

BRIEF DESCRIPTION OF THE DRAWINGS

An embodiment of the present invention will now be described, by way of example only, with reference to the accompanying drawings, in which:

FIG. 1 is a plan view of a skin marker according to a first embodiment of the present invention;

FIG. 2 is a side view of the skin marker of FIG. 1;

FIG. 3 is a plan view of a skin marker according to an alternative embodiment of the present invention;

FIG. 4 is a plan view of a skin marker according to a further alternative embodiment of the present invention, with various surface patterns;

DETAILED DESCRIPTION OF THE PREFERRED EMBODIMENTS

Figure 6:
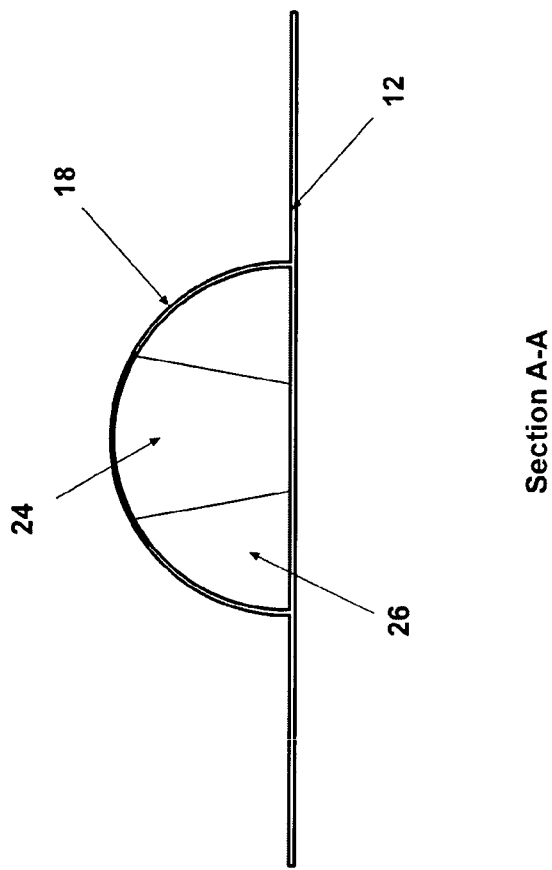
FIG. 6 is a sectional view through the skin marker of FIG. 5 on line A-A.

The skin marker 10 is made from 0.125 mm thick polycarbonate (PC) or polyester (PET) film (or a comparable flexible carrier suitable for graphic printing) comprising a circular central portion 12 and having two or more radially extending attachment wings or tabs 14 provided to allow the marker to be attached to the skin. The tabs 14 may be coated with a suitable adhesive, such as a hypoallergenic pressure sensitive adhesive (for example Duplomed 2806), which may be covered by a protective releasable covering, or may simply be used to receive surgical tape to secure the marker to the skin, particularly in areas of excessive hair. As shown in FIGS. 1, 3, and 4, different versions of the marker 10 may be produced having a different number of tabs 14 to suit different anatomical locations on the body of the patient. The tri-form shape shown in FIG. 4 may provide the best adhesion on most locations. However, any other number or arrangement of tabs may be provided to suit the location to which the marker is to be attached. Unevenly spaced or odd numbered tabs may be provided to provide a better distribution of forces at particular locations.

The width of each tab 14 is reduced at the junction of the tab 14 with the central portion 12 of the marker by means of cut-outs 16 to provide a hinge joint for flexion. This assists the central circular portion 12 of the marker 10 to retain its profile and provides enhanced adhesion at this area. The distal ends of the tabs 14 are wider to provide a greater surface area for adhesion.

A raised hemispherical dome 18 is formed in the centre of the marker 10, such as shown in FIGS. 1 and 2. The dome 18 may have a diameter of between 5 mm and 25 mm, although a prototype has been made with a 10 mm diameter dome. The dome 18 comprises a hollow body encapsulating an oil based liquid or PVA hydrogel containing substances or additives which have a desired combination of radiance and/or hydration and/or radiopaque and/or radio luminescent properties and/or radioactive properties. These substances can be imaged using ionizing radiation, electro-magnetic fields and the hemispherical form of the dome can be recognised by ultrasound and/or 3D surface scanning processes, including photogrammetry and laser scanning. For example, such substances may comprise Barium Sulphate to be recognisable by X-Ray techniques and/or all forms of gadolinium, such as a salt, a covalently bound compound, lattice or co-ordination complex, a chelate or ionic solution, to be recognised by MRI techniques. Chelates may be ustilised (e.g. Gadolinium III Chelate) to enhance the water solubility and reduce toxicity of such substances. The oil based liquid may comprise a mineral oil or any other liquid hydrocarbon oil of synthetic or natural origin, which may be cross-linked or thickened with styrenic copolymer, such as polystyrene blocks and/or rubber blocks (comprising polybutadiene, polyisoprene or their hydrogenated equivalents). In a particular example the liquid within the dome may comprise a paraffin based cross-linked hydrogel.

The dome 18, containing a liquid/gel, may have an embodiment where both are (at least in part) transparent whereby the dome may function as a lens, magnifying the skin location upon which the marker 10 is placed. For example, such magnifying effect may assist in locating the marker over a cross or other mark previously placed on the skin to assist accurate placement of the marker.

Figure 5:
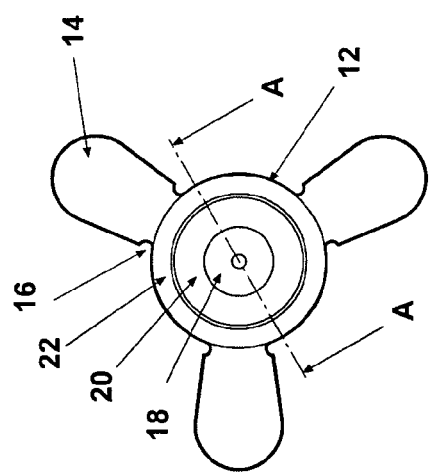
FIG. 5 is a plan view of a skin marker according to a further embodiment of the present invention.

In a modified embodiment shown in FIGS. 5 and 6, to preserve the lens effect with the use of radiopaque substances within the dome 18 (which are visually opaque), a conical section 24 of the dome 18 may be moulded with a non-radiopaque transparent material, as shown in FIG. 6. This maintains the sphere-like reference of radiopaque substance 26.

In an alternative embodiment the dome 18 may be coloured or patterned to enhance its visibility. For example, the surface of the dome may be black, preferably matt black, to provide enhanced contrast and thus visibility.

A coloured graphic surface image 20 (preferably blue or green) is formed on the central portion 12 of the marker 10 around the dome 18 for recognition by colour imaging processes, such as Red, Green and Blue (RGB) or Cyan, Yellow, Magenta and Key (CYMK) colour recognition algorithms. Using pixel recognition methods similar to "blue screen technology", the coloured graphic image 20, in a colour absent from the human body, can be isolated using video and still image processing systems. In the embodiment shown, the coloured graphic image 20 comprises a coloured ring arranged concentrically around the dome 18.

A further printed surface image 22, in the preferred embodiment in the form of a matt black ring surrounding the coloured graphic image 20, is provided on the central portion of the marker for recognition by Moiré Fringe 3D scanning processes or other optical scanning processes. The substantially non-reflective black pattern of the image 22 absorbs the light from an optical scanning process, resulting in a gap/blank on the surface model geometry. This gap clearly highlights the location of the 3D dome of the marker, which may also be detected as a 3D surface feature. The geometric centre of the dome 18 can thereby be easily calculated using simple algorithms.

Thus the present invention provides a skin reference marker that can be recognised by multi-modal imaging processes to assist diagnosis and operative planning. The skin markers may be used to identify regions for reference purposes and for image registration (for example for registering or aligning multiple images produced by different imaging techniques). The skin marker in accordance with the present invention allows a more seamless workflow and better image registration across a wider range of modalities than presently available.

The present invention also provides a skin marker that can be more easily, reliably and accurately placed on the skin of the patient by means of the radially extending attachment wings. This design does not depress the skin surface.

The invention is not limited to the embodiment(s) described herein but can be amended or modified without departing from the scope of the present invention. The present invention is not limited to the imaging modalities described above and encompasses other substances recognisable by other imaging modalities beyond the aforementioned modalities.

The invention claimed is:

1. A skin marker for providing a reference point for a plurality of different medical imaging procedures, said marker comprising:
   at least one substance having one or more properties chosen from (i) radiance, (ii) hydration, (iii) radiopaqueness, (iv) radio luminescence, and (v) radioactivity, for detection by one or more of (i) X-ray, (ii) Computer Tomography (CT), (iii) MRI, (iv) Ultrasonic scanning processes, and (v) Positron Emission Tomography (PET);

at least one first marking comprising a substantially non-reflective marking that is recognisable by Moiré Fringe 3D scanning processes; and at least one second marking comprising a coloured marking recognizable by a colour recognition imaging process;

wherein said at least one first marking is distinguishable from said at least one second marking by the Moiré Fringe 3D scanning processes, and wherein said at least one second marking is distinguishable from said at least one first marking by the colour recognition imaging process.

2. A skin marker as claimed in claim 1, wherein said at least one substance comprises a radiopaque material having a radiographic density sufficient to produce a discernable pattern on a radiographic image.

3. A skin marker as claimed in claim 1, wherein the marker includes a 3D surface formation.

4. A skin marker as claimed in claim 3, wherein said at least one substance is encapsulated within said 3D surface formation.

5. A skin marker as claimed in claim 3, wherein said 3D surface formation comprises a dome shaped member defining a substantially hemi-spherical surface formation.

6. A skin marker as claimed in claim 5, wherein said dome shaped member is located on a central portion of the marker.

7. A skin marker as claimed in claim 5, wherein at least a portion of the dome shaped member comprises an optically transparent magnifying lens to assist correct location of the marker on a skin surface.

8. A skin marker as claimed in claim 3, wherein the 3D surface formation is coloured and is provided with markings to provide enhanced visibility.

9. A skin marker as claimed in claim 3, wherein said 3D surface formation comprises a hollow body for containing said at least one substance, and wherein said at least one substance comprises a liquid, a semi-liquid or a solid material.

10. A skin marker as claimed in claim 9, wherein said material comprises one or more of (i) an oil based liquid, (ii) an oil-based semi-solid material, or (iii) a gelled material.

11. A skin marker as claimed in claim 10, wherein said material comprises said gelled material, said gelled material comprising an oil or aqueous base having a rheological structure, achieved by way of (i) high polymeric concentration, (ii) incorporation of stiffening agents, (iii) induced hydrogen bonding, or (iv) covalent cross-linking using molecular or ionic species.

12. A skin marker as claimed in claim 3, wherein said at least one marking comprises one or more concentric rings or ring-like markings located around said 3D surface formation.

13. A skin marker as claimed in claim 1, wherein the skin marker further comprises two or more tabs or wings to enable the marker to be attached to a person's body.

14. A skin marker as claimed in claim 13, wherein said tabs or wings extend radially from a central portion of the marker.

15. A skin marker as claimed in claim 13, wherein said tabs or wings are provided with a suitable adhesive to enable the marker to be affixed to a skin surface.

16. A skin marker as claimed in claim 15, wherein said adhesive is covered by a releasable cover material.

17. A skin marker as claimed in claim 13, wherein said tabs or wings define locations or carriers for the attachment of surgical tape to enable the marker to be affixed to a skin surface.

18. A skin marker as claimed in claim 13, wherein each of said tabs or wings comprises an indent or reduced width region at a neck of said tab or wing to increase flexion of said tab or wing.

19. A skin marker as claimed in claim 1, wherein said first marking comprises a matt black printed marking.

20. A skin marker as claimed in claim 1, wherein said second marking comprises a blue or green marking.

* * * * *